United States Patent
Stone et al.

(10) Patent No.: US 6,653,515 B2
(45) Date of Patent: Nov. 25, 2003

(54) SYNTHESIS OF α, β, β-TRIFLUOROSTYRENE VIA IN-SITU FORMATION OF TRIFLUOROVINYL METAL HALIDE

(75) Inventors: Charles Stone, West Vancouver (CA); Timothy J. Peckham, Richmond (CA); Donald J. Burton, Iowa City, IA (US); Anilkumar Raghavanpillai, Iowa City, IA (US)

(73) Assignee: Ballard Power Systems Inc., Burnaby (CA)

( * ) Notice: Subject to any disclaimer, the term of this patent is extended or adjusted under 35 U.S.C. 154(b) by 13 days.

(21) Appl. No.: 10/017,485

(22) Filed: Dec. 14, 2001

(65) Prior Publication Data

US 2003/0144439 A1 Jul. 31, 2003

(51) Int. Cl.$^7$ ........................... C07C 17/00; C07C 22/08
(52) U.S. Cl. ....................... 570/138; 570/126; 570/128; 570/144; 556/121; 526/75; 526/251; 525/276; 260/665 R
(58) Field of Search .................. 526/75, 251; 570/126, 570/128, 138, 144; 260/350 R, 665 R; 556/121; 525/276

(56) References Cited

U.S. PATENT DOCUMENTS

| | | | | |
|---|---|---|---|---|
| 2,612,528 A | | 9/1952 | Cohen | 260/651 |
| 2,651,627 A | | 9/1953 | Prober | 260/91.5 |
| 2,752,400 A | | 6/1956 | Prober | 260/651 |
| 2,874,166 A | | 2/1959 | Dixon | 260/346.1 |
| 3,449,449 A | | 6/1969 | Nichols et al. | 260/651 |
| 3,489,807 A | | 1/1970 | Shingu et al. | 260/649 |
| 4,605,685 A | * | 8/1986 | Momose et al. | 522/124 |
| 5,422,411 A | | 6/1995 | Wei et al. | 526/243 |
| 5,602,185 A | | 2/1997 | Stone et al. | 521/27 |
| 5,684,192 A | * | 11/1997 | Stone et al. | 562/826 |
| 5,834,523 A | | 11/1998 | Steck et al. | 521/27 |
| 6,350,925 B1 | * | 2/2002 | Tiers | 570/125 |

OTHER PUBLICATIONS

Anilkumar et al., "A Remarkable Room Temperature Preparation of the Trifluorovinylzinc Reagent from HFC–134a. A Cost–Effective, High Yield Synthesis of α,β,β–Trifluorostyrenes," Tetrahedron Letters 43, pp. 2731–2733, 2002.

Burdon, et al., "The Reactivity of the Hydrofluorocarbon 1,1,1,2–Tetrafluoroethane (HFC–134a) and Related Compounds Towards Base Attack. The Generation and Stability of the Tetrafluoroethyl, Trifluorovinyl and Related Anions," Journal of Fluorine Chemistry 99, pp. 127–131, 1999.

Banger et al., "Perfluorovinyl–metal derivatives: a new one–pot synthesis," Chem. Commun. 1:139–140, 1997.

Burdon et al., The Hydrofluorocarbon 1,1,1,2–tetrafluoroethane (HFC–134a) as a ready source of trifluorovinyllithium, Chem. Commun. 1: 49–50, 1996.

Burton et al., "Fluorinated Organometallics: Vinyl, Alkynyl, Allyl, Benzyl, Propargyl and Aryl Fluorinated Organometallic Reagents in Organic Synthesis," Tetrahedron 50(10):2993–3063, 1994.

Gillet et al., "Preparation et Reactivite de Fluorovinylzincs," Tetrahedron Letters 26(33):3999–4002, 1985.

Gillet et al., "Preparation and Reactivity of Fluorovinylzincs," CAS Abstract, Accession No. 1986:406588, 1985.

Hansen et al., "The Stereospecific Preparation of Fluorinated Vinyl Zinc Reagents from Polyfluorinated Vinyl Iodides or Bromides and Zinc Metal," J. Fluorine Chemistry 35: 415–420, 1987.

Heinze and Burton, "Palladium–Catalyzed Cross–Coupling of Perfluoroalkenylzinc Reagents with Aryl Iodides. A New, Simple Synthesis of α,β,β–Trifluorostyrenes and the Stereoselective Preparation of 1–Arylperfluoropropenes," J. Org. Chem. 53:2714–2720.

Heinze and Burton, "Palladium Catalyzed Coupling of F–Vinyl Zinc Reagents with Aryl Iodides. An Improved Synthesis of α,β,β–Trifluorostyrenes and the Stereospecific Preparation of 1–Phenyl–F–Propenses," J. Org. Chem. 31:115–119, 1986.

Sorokina et al., "Synthesis of Trifluorostyrene and its Derivatives by Reaction of Trifluorovinyltetramethyltin with Aryl Iodides in the Presence of Palladium Complexes," translated from Zhurnal Organicheskoi Khimii 18(11):2458–2459, Nov. 1982.

* cited by examiner

Primary Examiner—Fred Teskin
(74) Attorney, Agent, or Firm—Seed IP Law Group PLLC

(57) ABSTRACT

α,β,β-Trifluorostyrene and derivatives thereof synthesized in two steps from 1,1,1,2-tetrafluoroethylene. In the first step, 1,1,1,2-tetrafluoroethylene is reacted with a base, a metal salt such as zinc chloride and an optionally amine to form a trifluorovinyl metal complex. In the second step, the trifluorostyrene or derivative is obtained by reacting the trifluorovinyl metal complex with an aryl transfer agent such as, for example, an aryl triflate or an aryl halide, in the presence of a metal catalyst and optionally a coordinating ligand. Both steps may be carried out in one reactor.

33 Claims, No Drawings

SYNTHESIS OF α, β, β-TRIFLUOROSTYRENE VIA IN-SITU FORMATION OF TRIFLUOROVINYL METAL HALIDE

BACKGROUND OF THE INVENTION

1. Field of the Invention

This invention relates to a method for the synthesis of α,β,β-trifluorostyrene and related monomers via the in-situ formation of a trifluorovinyl metal complex.

2. Description of the Related Art

α,β,β-Trifluorostyrenes ("TFS") can be used as monomers in the production of polymers that, in turn, can be used to produce membranes with favorable chemical and mechanical properties. In addition, if the resultant polymers are functionalized with an ion-exchange group, they can be used to form ion-exchange membranes. A polymer membrane comprising TFS and/or substituted TFS monomer units may be suitable for a wide variety of applications and, in particular, such polymer membranes containing ion-exchange functionality have been used in electrochemical applications such as fuel cells as disclosed in U.S. Pat. Nos. 5,422,411, 5,602,185 and 5,834,523.

The synthesis of α,β,β-trifluorostyrene was initially reported in the late 1940's and early 1950's. While several methods have since been reported, none of the methods are economically viable in the large scale synthesis of TFS and related monomers. Typical conditions that could render methodologies generally unsuitable for large scale synthesis include low yields, high or low temperatures, high pressures, the use of toxic chemicals and the use of environmentally damaging chemicals such as chlorofluorocarbons ("CFCs").

U.S. Pat. No. 2,612,528 discloses a multi-step synthesis of TFS via a Friedal-Crafts acylation to produce an overall TFS yield of about 30%. In addition to the low yield obtained, the method also requires the use of a toxic fluorinating agent, namely antimony pentafluoride, and the isolation of CFC intermediates.

U.S. Pat. Nos. 2,651,627 and 2,752,400 report a synthesis of TFS from chlorotrifluoroethylene and benzene by pyrolysis at 550–600° C. Not only does this method require high temperatures and the use of a CFC as a starting material, but this method only results in low yields of less than 30%. Pyrolysis at 600–800° C. was also reported in U.S. Pat. No. 3,489,807 in the synthesis of TFS from β,β-chlorofluoroethylbenzene and 2-chloro-1,1-difluoroethylene, though, relatively low yields were similarly reported. Low yields also result from the synthesis of TFS via the reaction of phenyl lithium with tetrafluoroethylene as disclosed in U.S. Pat. No. 2,874,166. Cryogenic temperatures of −30 to −100° C. are disclosed in U.S. Pat. No. 3,449,449 for the reaction of solid phenylsodium with tetrafluoroethylene under high pressure (i.e., 70–1400 kPa) to form TFS.

Relatively high yields at mild temperatures are described in Heinze and Burton (*Journal of Organic Chemistry* 53:2714–2720, 1998) for the synthesis of TFS. However, this synthesis requires the use of either iodotrifluoroethylene or bromotrifluoroethylene as a starting material. Bromo- and iodotrifluoroethylene are class 2 ozone-depleters that are both relatively expensive and currently commercially available in large volumes from only one source in North America, namely Halocarbon Products Corporation.

Accordingly, there remains a need for improved synthetic methods for making TFS and related monomers, particularly methods that provide for relatively high yields under mild conditions using commercially available and relatively environmentally benign starting materials.

BRIEF SUMMARY OF THE INVENTION

The present method provides for the two-step synthesis of TFS or a derivative thereof from 1,1,2-tetrafluoroethane ("HFC-134a").

In the first step, a trifluorovinyl metal complex is formed by effecting a reaction between HFC-134a, an amine, a base and a metal salt. This is shown in the following reaction wherein $MX^1_n$ is the metal salt:

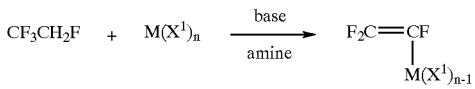

The amine may be added to the reaction mixture as a free amine or with the metal salt in a preformed metal salt-amine complex. Alternatively, the amine may be generated in situ. For example, if lithium diisopropylamide is used as the base, diisopropylamine will be generated in situ.

In another embodiment of the first step, a trifluorovinyl metal complex is formed by effecting a reaction between HFC-134a, a base and a metal salt, wherein the reaction temperature is greater than −68° C. In a more specific embodiment, the reaction temperature is from about 15° C. to about 25° C.

The second step involves reacting the trifluorovinyl metal complex, as prepared above, with an aromatic transfer agent ($ArX^2$) in the presence of a metal catalyst and a coordinating ligand to form TFS or a derivative thereof. This is shown in the following reaction:

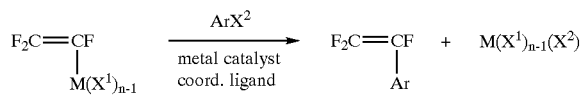

The $X^2$ group of the aromatic transfer agent can be any of a variety of suitable transfer agent leaving groups, such as halogen, triflate (i.e., $-OSO_2CF_3$), or other suitable groups known to those skilled in the art. In this regard, higher yields have been observed with aromatic iodides. Typically, the aromatic group will be a carbocyclic aromatic group, such as phenyl or naphthyl, although heterocyclic aromatic groups, such as thienyl, may also be used. As discussed in greater detail below, the aromatic transfer agent may be optionally substituted.

To form TFS, the aromatic transfer agent is a phenyl halide (such as phenyl iodide). The metal catalyst may be palladium, nickel or platinum, in either the zero oxidation state or reduced to this oxidation state in situ. Palladium(0) bis(dibenzylidene acetone) is an example of a metal catalyst that is easy to handle and both temperature and air stable. The coordinating ligand can be a mono- or multidentate phosphine, arsine or other ligand known to those skilled in the art. The ligand may be, for example, triphenylphosphine.

The two steps in the synthesis of TFS or derivative thereof can be performed without isolating the trifluorovinyl metal complex intermediate. Further, a mixture of two or more TFS monomers (or derivatives thereof) can be synthesized by adding a second aromatic transfer agent along with the first aromatic transfer agent.

These and other aspects of the invention will be evident upon reference to the following detailed description.

DETAILED DESCRIPTION OF PREFERRED EMBODIMENTS

α,β,β-Trifluorostyrene (TFS) has the following structure (I):

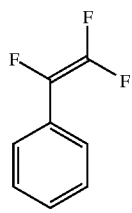

As used herein, "derivatives" of TFS include compounds having the following structure (II):

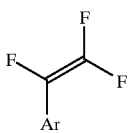

wherein Ar represents an aromatic carbocyclic or heterocylic moiety, optionally substituted with one or more substituents, but not including structure (I). Representative aromatic carbocylic moieties include phenyl and 1- and 2-naphthyl, while representative aromatic heterocyclic moieties include thienyl, furyl and pyrrolyl. When substituted by two or more substituents, the substituents may be the same or different. Substituents include any moiety not having acidic hydrogens. Representative substituents include, but are not limited to, hydroxy, cyano, nitro, halo, halogenated alkyl such as trifluoromethyl, halogenated alkenyl such as —CF=CF$_2$, alkoxy such as methoxy, and aryloxy such as phenoxy.

As used herein, "alkyl" means a straight chain or branched, noncyclic or cyclic, unsaturated or saturated aliphatic hydrocarbon containing from 1 to 10 carbon atoms. Representative saturated straight chain alkyls include methyl, ethyl, n-propyl, n-butyl, n-pentyl, n-hexyl, and the like; while saturated branched alkyls include isopropyl, sec-butyl, isobutyl, tert-butyl, isopentyl, and the like. Representative saturated cyclic alkyls include cyclopropyl, cyclobutyl, cyclopentyl, cyclohexyl, —CH$_2$cyclopropyl, —CH$_2$cyclobutyl, —CH$_2$cyclopentyl, —CH$_2$cyclohexyl, and the like; while unsaturated cyclic alkyls include cyclopentenyl and cyclohexenyl, and the like. Cyclic alkyls, also referred to as "homocyclic rings," and include di- and poly-homocyclic rings such as decalin and adamantyl. Unsaturated alkyls contain at least one double or triple bond between adjacent carbon atoms (referred to as an "alkenyl" or "alkynyl", respectively). Representative straight chain and branched alkenyls include ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like; while representative straight chain and branched alkynyls include acetylenyl, propynyl, 1-butynyl, 2-butynyl, 1-pentynyl, 2-pentynyl, 3-methyl-1 butynyl, and the like.

Furthermore, "aryl" means an aromatic carbocyclic moiety, such as phenyl and naphthyl, while "alkoxy" and "aryloxy" mean —O-alkyl and —O-aryl, respectively.

In the present approach, 1,1,1,2-tetrafluoroethane ("HFC-134a") is used as a starting material in the synthesis of TFS, or a derivative thereof, under relatively mild conditions. As a starting material, HFC-134a is economical and environmentally benign. HFC-134a has been reported as a starting material for perfluorovinyl-metal derivatives in Banger et al. (*Chemical Communications* 1997, 139–140). However, Banger et al. use very low temperatures (i.e., −78° C.) for the synthesis of the perfluorovinyl metal derivatives as it was understood that trifluorovinyl lithium decomposes at higher temperatures (see, e.g., D. J. Burton et al., *Tetrahedron*, 2993, 1994).

In an embodiment of the present method, TFS monomers and derivatives thereof can be synthesized in two steps. In the first step, a trifluorovinyl metal complex is formed by reacting HFC-134a with a base, an amine and a metal salt. In the second step, an aromatic transfer agent, a metal catalyst and a coordinating ligand are combined and heated. After cooling to room temperature, TFS monomers, or derivatives thereof, can typically be isolated in yields of about 75–85%.

It should be understood that various bases may be used in this first step, provided that the base is capable of deprotonating HFC-134a. Representative bases include, but are not limited to, alkyl and aryl lithium reagents (such as lithium diisopropylamide or t-butyllithium), alkyl and aryl Grignard reagent, and sodium or potassium metals.

Representative metal salts, $M(X^1)_n$, include, but are not limited to, zinc salt, mercuric salt, indium salt, magnesium salt, cadmium salt, thallium salt, alkyl tin salt, aryl tin salt, alkyl lead salt or aryl lead salt. The metal salt may be a metal halide (i.e., $X^1$=halide) wherein the halide is a chloride, bromide or iodide, although other metal salts such as a metal acetate ($X^1$=acetate) or a metal triflate ($X^1$=triflate) may also be used. Also, the $X^1$ groups need not be the same, although they typically are the same, and n represents the number of electron donating $X^1$ groups are associated with the metal M. The metal salt is preferably anhydrous, though small amounts of water may be present. Nevertheless, higher yields tend to be observed in the absence of water during the first step. Anhydrous zinc chloride is a representative reagent as it reacts efficiently, and it is more economical and/or more environmentally benign than the other salts mentioned above.

Suitable amines include alkyl, aryl and heteroaromatic amines as understood by those skilled in the art. In this regard, "heteroaromatic amine" means an aromatic heterocycle ring of 5 to 10 members and having at least one nitrogen atom and containing at least 1 carbon atom, including both mono- and bicyclic ring systems. Representative heteroaromatic amines include (but are not limited to) pyrrole, indole, azaindole, pyridine, quinoline, isoquinoline, pyrazole, imidazole, benzimidazole, pyridazine, pyrimidine, pyrazine, cinnoline, phthalazine, and quinazoline.

Further, the amine may be mono- or multi-dentate. Without limiting the generality of the foregoing, the amine may be, for example, tetramethylethylenediamine ("TMEDA"), diisopropylamine, triethylamine, or 2,2'-bi-pyridyl. Alternatively, the amine need not be independently added to the reaction mixture, though either lower yields tend to be observed or the reaction must be operated at lower temperatures. Nevertheless, acceptable yields may still be observed at temperatures higher than −68° C. even without any amine being present in the reaction mixture. However, if lithium diisopropylamide ("LDA") is used as the base, relatively high yields are observed at higher temperatures even without amine being independently added to the reaction mixture. Without being bound by theory, it is believed that higher yields are observed due to an amine, namely diisopropylamine, being generated in situ as LDA reacts with HFC-134a.

The amine and the metal salt can be added to the reaction mixture as separate components, or in the form of a preformed metal salt-amine complex, such as, for example, a $ZnCl_2 \cdot TMEDA$ complex.

THF is used as a solvent in the above embodiment though it is understood that other solvents may be used.

Dependent on the base chosen, the temperature of the reaction to form the trifluorovinyl metal complex may be varied without significantly affecting the yield. For example, the reaction may be performed at room temperature (i.e. 15–25° C.) and also at low temperatures, such as, for example −90° C. without significantly impacting the yield. However, an advantage of the present method is that it allows more practical conditions to be used in the synthesis of TFS monomers and derivatives thereof.

The aromatic transfer agent ($ArX^2$) may be an aromatic halide (i.e., $X^2$=fluoro, chloro, bromo or iodo), triflate (i.e., $X^2$=—$OSO_2CF_3$), or other aromatic transfer agent known to those skilled in the art. The aryl group is phenyl to yield TFS. Alternatively, to yield TFS derivatives, the aromatic group may be substituted phenyl, naphthyl, substituted naphthyl, heteroaryl or substituted heteroaryl. To this end, "heteroaryl" means an aromatic heterocycle ring of 5 to 10 members and having at least one heteroatom selected from nitrogen, oxygen and sulfur, and containing at least 1 carbon atom, including both mono- and bicyclic ring systems. Representative heteroaryls include (but are not limited to) furyl, benzofuranyl, thiophenyl, benzothiophenyl, pyrrolyl, indolyl, isoindolyl, azaindolyl, pyridyl, quinolinyl, isoquinolinyl, oxazolyl, isooxazolyl, benzoxazolyl, pyrazolyl, imidazolyl, benzimidazolyl, thiazolyl, benzothiazolyl, isothiazolyl, pyridazinyl, pyrimidinyl, pyrazinyl, triazinyl, cinnolinyl, phthalazinyl, and quinazolinyl.

Furthermore, a combination of different aromatic transfer agents may be added to the reaction mixture to yield a mixture of TFS monomers and/or derivatives thereof. For example, if the aromatic transfer agent is iodophenyl and iodophenyl substituted with trifluoromethyl (at either the ortho, meta or para position), and such transfer agents are added together as the aromatic transfer agents, a mixture of TFS and $F_3CC_6H_4CF$=$CF_2$ will be generated.

The metal catalyst can be any palladium, nickel or platinum metal catalyst wherein the metal is in the zero oxidation state. Alternatively, the metal catalyst may be in the +2 or +4 oxidation state and then reduced in situ, to the zero oxidation state. For example, the metal catalyst may be palladium bis(dibenzylidene acetone).

The coordinating ligand may be any ligand selected from the group of mono or multidentate phosphines and arsines. High yields of TFS and derivatives thereof may still be observed if the coordinating ligand is not added to the reaction mixture. Triphenylphosphine as the coordinating ligand allows high yields of TFS and derivatives thereof, is cost effective and relatively environmentally benign.

A small amount of bis trifluorometal complex may be formed in the first step along with the "mono-complex". This is shown in the following schematic:

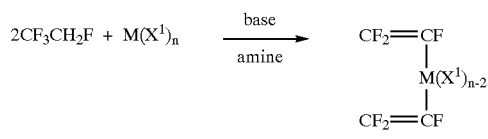

The formation of the "bis complex" is not significant as it reacts with the aromatic transfer agent, similarly to the mono complex in the second step of the reaction to produce TFS or derivative thereof.

The isolation and purification of TFS and derivatives can be accomplished by, for example, first flash distilling the reaction mixture under vacuum to separate the solvents and product from the metal salts produced during the reaction. The TFS monomer may then be isolated by fractional distillation under partial pressure. Depending on the relative volatility of the solvent, the TFS or related monomer may be isolated directly from the reaction mixture by fractional distillation.

The monomer may then be polymerized to form a polymer suitable for use in such applications as a membrane in electrochemical fuel cells. The polymer may be a homopolymer or a copolymer. Copolymers may be random, block or graft copolymers.

EXAMPLE 1

Trifluorovinyl Zinc Chloride

A 250 mL three-necked round bottom flask fitted with a dry ice/isopropanol condenser, septum and a low temperature thermometer were assembled while hot and flushed with nitrogen gas. It was charged with $ZnCl_2$ (3.42 g, 25.0 mmol) and THF (15.0 ml). The solution was cooled to 12–15° C. using a cold water bath and gaseous HFC-134a (2.5 ml, 30.0 mmol) was condensed in the saturated solution. LDA was added to the reaction mixture slowly over 35 min. through a cannula while maintaining the temperature between 15 and 20° C. The tip of the cannula was dipped below the surface of the solution to avoid decomposition of the intermediate vinyl lithium at the tip by the reaction of gaseous HFC-134a with LDA. The reaction mixture was stirred for 1 h at 20° C. and then allowed to settle for 2 h. The $^{19}F$ NMR of the zinc reagent was recorded at this stage and showed formation of the trifluorovinyl zinc complex along with traces of unreacted HFC-134a. Small amounts of bis trifluorovinyl zinc product was also formed along with mono trifluorovinyl zinc complex as seen by the shoulder peaks in the up field direction to the mono complex. The ratio of mono/bis was approximately 90:10. The estimated yield of the trifluorovinyl zinc chloride was 73%.

EXAMPLES 2–9

Following the general procedure as provided for in Example 1, the reaction was repeated varying the base, the metal salt, the amine and/or the temperature as provided for in the following table.

| No | Base | $M(X^1)_n$ | Amine | Temp | Yield |
|---|---|---|---|---|---|
| 2 | LDA | $ZnCl_2$ | TMEDA | 20° C. | 76% |
| 2 | LDA | $ZnCl_2$ | TMEDA | 20° C. | 76% |
| 3 | LDA | $ZnCl_2$ | diisopropylamine | 20° C. | 75% |
| $4^a$ | LDA | $ZnCl_2$ | TMEDA | −26° C. | 84% |
| $5^b$ | LTMP | $ZnCl_2$ | TMEDA | 20° C. | 82% |
| 6 | t–BuLi | $ZnI_2$ | none | −58° C. | 76% |

-continued

| No | Base | M(X¹)ₙ | Amine | Temp | Yield |
|---|---|---|---|---|---|
| 7 | LDA | ZnI$_2$ | none added | −26° C. | 58% |
| 8 | LDA | ZnI$_2$ | TMEDA | −26° C. | 83% |
| 9[£] | LTMP | Bu$_3$SnCl | none | −26° C. | 68% |

[a]The metal salt and amine were added as a preformed ZnCl$_2$ · TMEDA complex.
[b]LTMP is lithium-2,6-tetramethyl-4-methoxy piperide. The structure of LTMP is:

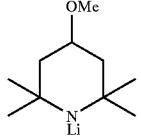

EXAMPLE 10

General Procedure For TFS And Derivatives

Trifluorovinyl zinc chloride was prepared according to Example 1. The dry ice/isopropanol condenser and the thermometer from the reaction described in Example 1 were replaced with a stopcock and stopper. The trifluorovinyl zinc chloride solution was concentrated under vacuum to almost half its original volume. During this concentration, excess HFC-134a was evaporated off. After careful displacement of the vacuum with nitrogen, a condenser fitted with a nitrogen inlet replaced the stopcock. Iodobenzene (approx. 0.8 eq) and tetrakistriphenylphosphine palladium (Pd(PPh$_3$)$_4$) (approx. 1.5 mol %) were then added. The reaction mixture was heated at 60° C. using an oil bath. The reaction progress was monitored using $^{19}$F NMR by sampling small aliquots of the reaction mixture. After the complete conversion of the trifluorovinyl zinc chloride to the TFS, the reaction mixture was triturated several times with pentane or hexane and the combined extracts evaporated on a rotary evaporator after the addition of silica gel. Silica gel was added prior to evaporation of the solvent to absorb the TFS product and thereby prevent loss of product due to its volatile nature. After evaporation of the solvent, column chromatography on silica gel was then carried out with either pentane or hexane as eluent depending on the volatility of the TFS.

EXAMPLES 11–21

Following the general procedure as provided for in Example 10, the reaction was repeated varying the aryl halide.

| No. | ArX² | Product | Yield |
|---|---|---|---|
| 11 | iodophenyl | TFS | 69% |
| 12 | 1-iodo-4-nitrophenyl | p-O$_2$NC$_6$H$_4$CF=CF$_2$ | 37% |
| 13 | 1-iodo-4-trifluoromethylphenyl | p-F$_3$CC$_6$H$_4$CF=CF$_2$ | 66% |
| 14 | 1-iodo-3-trifluoromethyl phenyl | m-F$_3$CC$_6$H$_4$CF=CF$_2$ | 67% |
| 15 | 1-iodo-2-trifluoromethylphenyl | o-F$_3$CC$_6$H$_4$CF=CF$_2$ | 67% |
| 16 | 4-iodoanisole | p-MeOC$_6$H$_4$CF=CF$_2$ | 82% |
| 17 | 3-iodoanisole | m-MeOC$_6$H$_4$CF=CF$_2$ | 85% |
| 18[a] | 1-bromo-4-iodophenyl | p-BrC$_6$H$_4$CF=CF$_2$ | 75% |
| 19[a] | 1,4-di-iodo-phenyl | p-F$_2$C=FCC$_6$H$_4$CF=CF$_2$ | 71% |
| 20 | 1-iodo-naphthalene | C$_{10}$H$_7$CF=CF$_2$ | 83% |
| 21 | 2-iodo-thiophene | 2-(1,1,2-trifluorovinyl) thiophene | 59% |

[a]Instead of heating the reaction mixture at 60–70° C. as in the general procedure, the mixture was stirred at room temperature until the reaction was substantially complete.

While particular steps, elements, embodiments and applications of the present invention have been shown and described, it will be understood, of course, that the invention is not limited thereto since modifications may be made by persons skilled in the art, particularly in light of the foregoing teachings. It is therefore contemplated by the appended claims to cover such modifications as incorporate those steps or elements that come within the spirit and scope of the invention.

What is claimed is:

1. A method for preparing a trifluorovinyl metal complex comprising effecting a reaction between 1,1,1,2-tetrafluoroethane, an amine, a base, and a metal salt, wherein the amine is an alkyl amine, an aryl amine or an heteroaromatic amine.

2. The method of claim 1 wherein the amine is a multidentate alkyl amine.

3. The method of claim 2 wherein the amine is tetramethylethylenediamine.

4. The method of claim 1 wherein the amine is generated in situ.

5. The method of claim 1 wherein the base is lithium diisopropylamide, t-butyl lithium or lithium-2,6-tetramethyl-4-methoxy piperide.

6. The method of claim 5 wherein the base is lithium diisopropylamide.

7. The method of claim 1 wherein the metal salt is a metal halide.

8. The method of claim 7 wherein the metal halide is a zinc halide.

9. The method of claim 8 wherein the zinc halide is anhydrous zinc chloride.

10. The method of claim 1 wherein the metal salt and the amine are in a preformed metal salt-amine complex.

11. The method of claim 1 wherein the reaction temperature is from about 15 to about 25° C.

12. A method for preparing a trifluorovinyl metal complex comprising effecting a reaction between 1,1,1,2-tetrafluoroethane; a base; and a metal salt wherein the reaction temperature is greater than −68° C.

13. The method of claim 12 wherein the base is lithium diisopropylamide, t-butyl lithium or lithium-2,6-tetramethyl-4-methoxy piperide.

14. The method of claim 13 wherein the base is lithium diisopropylamide.

15. The method of claim 12 wherein the metal salt is a metal halide.

16. The method of claim 15 wherein the metal halide is zinc halide.

17. The method of claim 16 wherein the zinc halide is anhydrous zinc chloride.

18. The method of claim 12 wherein the effecting step further comprises an amine, wherein the amine is an alkyl amine, an aryl amine or a heteroaromatic amine.

19. The method of claim 18 wherein the metal salt and the amine are in a preformed metal salt-amine complex.

20. The method of claim 12 wherein the reaction temperature is from about 15 to about 25° C.

21. A method for preparing an α,β,β-trifluorostyrene monomer or derivative thereof, comprising the step of reacting the trifluorovinyl metal complex of any one of claims 1 or 12 with a first aromatic transfer agent in the presence of a metal catalyst.

22. The method of claim 21 wherein the first aryl transfer agent is an aryl triflate, an aryl iodide, an aryl bromide or an aryl chloride.

23. The method of claim 22 wherein the first aryl transfer agent is an aryl iodide.

24. The method of claim 23 wherein the aryl iodide is phenyl iodide.

25. The method of claim 21 wherein the reacting step further comprises a second aryl transfer agent, wherein the second aryl transfer agent is an aryl triflate, an aryl iodide, an aryl bromide or an aryl chloride.

26. The method of claim 21 wherein the metal catalyst is a palladium metal catalyst, a nickel metal catalyst or a platinum metal catalyst.

27. The method of claim 26 wherein the metal catalyst is palladium(0) bis(dibenzylidene acetone).

28. The method of claim 21 wherein the reacting step further comprises a coordinating ligand selected from the group consisting of a phosphine and an arsine.

29. The method of claim 28 wherein the coordinating ligand is triphenylphosphine.

30. A method for preparing a polymer, comprising the step of polymerizing the α,β,β-trifluorostyrene monomer or derivative thereof of claim 21.

31. The method of claim 30 wherein the polymer is a copolymer.

32. The method of claim 30 wherein the polymer is a random copolymer.

33. The method of claim 30 wherein the polymer is a graft copolymer.

* * * * *